United States Patent [19]
Flockerzi

[11] Patent Number: 6,008,215
[45] Date of Patent: Dec. 28, 1999

[54] BENZONAPHTHYRIDINES AS BRONCHIAL THERAPEUTICS

[75] Inventor: Dieter Flockerzi, Allensbach, Germany

[73] Assignee: Byk Gulden Lomberg Chemische Fabrik GmbH, Konstanz, Germany

[21] Appl. No.: 09/284,458

[22] PCT Filed: Nov. 5, 1997

[86] PCT No.: PCT/EP97/06096

§ 371 Date: Apr. 16, 1999

§ 102(e) Date: Apr. 16, 1999

[87] PCT Pub. No.: WO98/21208

PCT Pub. Date: May 22, 1998

[30] Foreign Application Priority Data

Nov. 11, 1996 [DE] Germany .......................... 196 46 298
Nov. 13, 1996 [DE] Germany .......................... 961 18 188
Sep. 5, 1997 [DE] Germany .......................... 197 39 056

[51] Int. Cl.$^6$ .......................... A61K 31/47; A61K 31/395; C07D 471/04; C07D 401/12
[52] U.S. Cl. .......................... 514/212; 514/232.8; 514/292; 540/597; 544/126; 546/81
[58] Field of Search .......................... 546/81; 514/292, 514/212, 232.8; 540/292; 544/126

[56] References Cited

U.S. PATENT DOCUMENTS 3,899,494 8/1975 Ott ..................................... 260/287 R

FOREIGN PATENT DOCUMENTS 247971 12/1981 European Pat. Off. .
91/17991 5/1991 WIPO .

*Primary Examiner*—Evelyn Mei Huang
*Attorney, Agent, or Firm*—Jacobson, Price, Holman & Stern, PLLC

[57] ABSTRACT

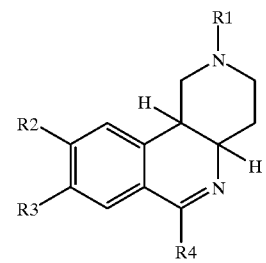

Compounds of formula (I) in which R1, R2, R3 and R4 have the meanings indicated in the description, are novel active bronchial therapeutics

13 Claims, No Drawings

BENZONAPHTHYRIDINES AS BRONCHIAL THERAPEUTICS

This application is the national phase of PCT/EP97/06096, filed Nov. 5, 1997, published as WO 98/21208 on May 22, 1998.

FIELD OF APPLICATION OF THE INVENTION

The invention relates to novel 6-phenylbenzonaphthyridines which are used in the pharmaceutical industry for the production of medicaments.

KNOWN TECHNICAL BACKGROUND

DE-A 21 23 328 and U.S. Pat. No. 3,899,494 describe substituted benzonaphthyridines which are distinguished by marked inhibition of blood platelet aggregation. EP 247 971 and WO 91/17991 disclose 6-phenyl-benzonaphthyridines for the treatment of inflammatory airway disorders.

DESCRIPTION OF THE INVENTION

It has now been found that the following compounds of the formula I which are described in greater detail and differ from the compounds of EP 247 971 or WO91/17991, in particular, by the substitution on the 6-phenyl ring, have surprising and particularly advantageous properties.

The invention thus relates to compounds of the formula I

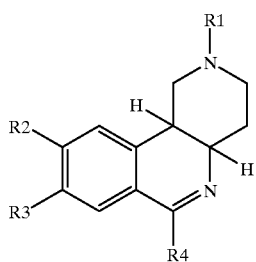

(I)

in which

R1 is 1–4C-alkyl,

R2 is hydroxyl, 1–4C-alkoxy, 3–7C-cycloalkoxy, 3–7C-cycloalkylmethoxy or 1–4C-alkoxy which is completely or predominantly substituted by fluorine, R3 is hydroxyl, 1–4C-alkoxy, 3–7C-cycloalkoxy, 3–7C-cycloalkylmethoxy or 1–4C-alkoxy which is completely or predominantly substituted by fluorine, or in which R2 and R3 together are a 1–2C-alkylenedioxy group, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-pyrrolidinyl, 1-piperidyl, 1-hexahydroazepinyl or 4-morpholinyl radical, and to the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1–4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned.

1–2C-Alkylenedioxy represents, for example, the methylenedioxy (—O—CH$_2$—O—) or the ethylenedioxy radical (—O—CH$_2$—CH$_2$—O—).

Halogen within the meaning of the invention is fluorine, chlorine or bromine.

1–8C-Alkoxy represents radicals, which, in addition to the oxygen atom, contain a straight-chain or branched alkyl radical having 1 to 8 carbon atoms. Examples which may be mentioned are the octyloxy, heptyloxy, hexyloxy, pentyloxy, methylbutoxy, ethylpropoxy, butoxy, isobutoxy, sec-butoxy, tert-butoxy, propoxy or, preferably, the isopropoxy, ethoxy or methoxy radical.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radical.

3–7C-Cycloalkyl represents the cyclopropyl, cyclobutyl, cyclopentyl, cyclohexyl or cycloheptyl radical.

3–7C-Cycloalkylmethyl represents a methyl radical which is substituted by one of the abovementioned 3–7C-cycloalkyl radicals. Examples which may be mentioned are the cycloalkylmethyl radicals cyclopropylmethyl, cyclobutylmethyl and cyclopentylmethyl.

Suitable salts of compounds of the formula I—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxylbenzoyl)benzoic acid, butyric acid, sutfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxyl-2-naphthoic acid, where the acids are employed in salt preparation—depending on whether a mono- or polybasic acid is concerned and depending on which salt is desired—in an equimolar quantitative ratio or one differing therefrom.

On the other hand—for example in the case of carboxyl substitution—salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which

R1 is 1–4C-alkyl,

R2 is 1–4C-alkoxy, 3–7C-cycloalkoxy, 3–7C-cycloalkylmethoxy or 1–2C-alkoxy which is completely or predominantly substituted by fluorine, R3 is 1–4C-alkoxy, 3–7C-cycloalkoxy, 3–7C-cycloalkylmethoxy or 1–2C-alkoxy which is completely or predominantly substituted by fluorine, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-piperidyl, 1-hexahydroazepinyl or 4-morpholinyl radical, and the salts of these compounds.

One embodiment of the compounds of the formula I to be emphasized are those compounds in which R1 is 1–4C-alkyl, R2 is 1–4C-alkoxy, 3–7C-cycloalkoxy, 3–7C-cycloalkylmethoxy or 1–2C-alkoxy which is completely or predominantly substituted by fluorine, R3 is 1–4C-alkoxy, 3–7C-cycloalkoxy, 3–7C-cycloalkylmethoxy or 1–2C-alkoxy which is completely or predominantly substituted by fluorine, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together and including the nitrogen atom to which both are bonded, are a 1-piperidyl or 1-hexahydroazepinyl radical, and the salts of these compounds.

Compounds of the formula I particularly to be emphasized are those in which

R1 is methyl,

R2 is 1–4C-alkoxy, 3–7C-cycloalkoxy or 1–2C-alkoxy which is completely or predominantly substituted by fluorine, R3 is 1–4C-alkoxy, 3–7C-cycloalkoxy or 1–2C-alkoxy which is completely or predominantly substituted by fluorine, R4 is a phenyl radical which is substituted by R5 and R6, where R5 is hydrogen, hydroxyl, 1–4C-alkyl or 1–4C-alkoxy, R6 is CO—R7 or CO—R8, where R7 is hydroxyl, 1–8C-alkoxy or 3–7C-cycloalkoxy and R8 is N(R81)R82, where R81 and R82 independently of one another are hydrogen, 1–7C-alkyl or 3–7C-cycloalkyl, or where R81 and R82, together and including the nitrogen atom to which both are bonded, are a 1-piperidyl, 1-hexahydroazepinyl or 4-morpholinyl radical, and the salts of these compounds.

One embodiment of the compounds of the formula I particularly to be emphasized are those compounds in which R1 is methyl, R2 is 1–4C-alkoxy, 3–7C-cycloalkoxy or 1–2C-alkoxy which is completely or predominantly substituted by fluorine, R3 is 1–4C-alkoxy, 3–7C-cycloalkoxy or 1–2C-alkoxy which is completely or predominantly substituted by fluorine, R4 is a phenyl radical which is substituted by R5 and R6, where R5 is hydrogen, hydroxyl, 1–4C-alkyl or i4C-alkoxy, R6 is CO—R7 or CO—R8, where R7 is hydroxyl, 1–8C-alkoxy or 3–7C-cycloalkoxy and R8 is N(R81)R82, where R81 and R82 independently of one another are hydrogen, 1–7C-alkyl or 3–7C-cycloalkyl, and the salts of these compounds.

Preferred compounds of the formula I are those in which

R1 is methyl,

R2 is methoxy or ethoxy,

R3 is methoxy or ethoxy,

R4 is a phenyl radical which is substituted by R5 and R6, where

R5 is hydrogen,

R6 is CO—R7 or CO—R8, where

R7 is hydroxyl or 1–8C-alkoxy and

R8 is N(R81)R82, where R81 and R82 independently of one another are hydrogen or 1–4C-alkyl or 5–7C-cycloalkyl, or where R81 and R82, together and including the nitrogen atom to which both are bonded, are a 1-piperidyl, 1-hexahydroazepinyl or 4morpholinyl radical, and the salts of these compounds.

One embodiment of the preferred compounds of the formula I are those compounds in which R1 is methyl, R2 is methoxy or ethoxy, R3 is methoxy or ethoxy, R4 is a phenyl radical which is substituted by R5 and R6,, where R5 is hydrogen, R6 is CO—R7 or CO—R8, where R7 is hydroxyl or 1–8C-alkoxy and R8 is N(R81)R82, where R81 and R82 independently of one another are hydrogen or 1–4C-alkyl, and the salts of these compounds.

Particularly preferred compounds of the formula I are those in which

R1 is methyl,

R2 is ethoxy,

R3 is methoxy or ethoxy,

R4 is a phenyl radical which is substituted by R5 and R6, where

R5 is hydrogen,

R6 is CO—R7 or CO—R8, where

R7 is 1–4C-alkoxy and

R8 is N(R81)R82, where R81 and R82 independently of one another are 1–4C-alkyl or -5–7C-cycloalkyl, or where R81 and R82, together and including the nitrogen atom to which both are bonded, are a 1-piperidyl or 1-hexahydroazepinyl radical, and the salts of these compounds.

The compounds of the formula I are chiral compounds having chiral centers in positions 4a and 10b

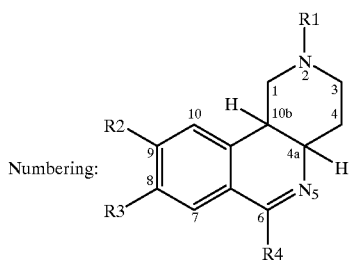

(I)

The invention therefore includes all conceivable pure diastereomers and pure enantiomers and mixtures thereof in any mixing ratio, including the racemates. Preferred are those compounds of the formula I in which the hydrogen atoms in positions 4a and 10b are in the cis position relative to one another. The pure cis enantiomers and their mixtures in any mixing ratio and including the racemates are particularly preferred here.

Particularly preferred in this connection are those compounds of the formula I which in positions 4a and 10b have the same absolute configuration as the compound (−)-cis-4-amino-3-(3,4-dimethoxyphenyl)-1-methylpiperidine dihydrochloride having the optical rotation $[\alpha]^{22}_D$ −57.1° (c=1, methanol) which can be employed as a starting material and is described in DE 42 17 401.

Especially to be emphasized are those compounds of formula I which can be prepared starting from the starting compounds (−)-cis-4-Amino-3-(3,4-diethoxyphenyl)-1-methylpiperidine dihydrochloride (example F) or (−)-cis-4-Amino-3-(3-ethoxy-4-methoxyphenyl)-1-methylpiperidine dihydrochloride (example O) and are selected from cis-8,9-Diethoxy-6-(4-isopropoxycarbonylphenyl)-2-methyl-1,2,3,4,4a,10b-hexahydrobenzo[c][1,6]-naphthyridine;

cis-8,9-Diethoxy-6-(4-diisopropylaminocarbonylphenyl)-2-methyl-1,2,3,4,4a-10b-hexahydrobenzo[c]-[1,6]naphthyridine;

cis-8,9-Diethoxy-6-(4-N-cyclohexyl-N-isopropylaminocarbonylphenyl)-2-methyl-1,2,3,4,4a,10b-hexahydrobenzo[c][1,6]naphthyridine;

cis-8,9-Diethoxy-6-(4-dibutylaminocarbonylphenyl)-2-methyl-1,2,3,4,4a,10b-hexahydrobenzo[c][1,6]-naphthyridine;

cis-8,9-Diethoxy-6-[4-(hexahydroazepin-1-yl-carbonyl)phenyl]-2-methyl-1,2,3,4,4a,10b-hexahydrobenzo[c][1,6] naphthyridine;

cis-8,9-Diethoxy-6-[4-(piperidin-1-ylcarbonyl)phenyl]-2-methyl-1,2,3,4,4a,10b-hexahydrobenzo[c][1,6]-naphthyridine;

cis-9-Ethoxy-8-methoxy-6-(4-diisopropylaminocarbonylphenyl)-2-methyl-1,2,3,4,4a,10b-hexahydrobenzo[c][1,6]naphthyridine;

cis-9-Ethoxy-8-methoxy-6-(4-dibutylaminocarbonylphenyl)-2-methyl-1,2,3,4,4a,10b-hexahydrobenzo-[c][1,6]naphthyridine;

cis-9-Ethoxy-8-methoxy-6-[4-(hexahydroazepin-1-yl-carbonyl)phenyl]-2-methyl-1,2,3,4,4a,10b-hexahydrobenzo[c][1,6]naphthyridine;

cis-9-Ethoxy-8-methoxy-6-[4-(piperidin-1-yl-carbonyl)phenyl]-2-methyl-1,2,3,4,4a,10b-hexahydrobenzo[c][1,6] naphthyridine and the salts of these compounds.

The enantiomers can be separated in a known manner (for example by preparation and separation of corresponding diastereoisomeric compounds) or by stereoselective synthesis methods. Such separation processes and synthesis methods are described, for example, in EP 247 971 and in DE42 17 401.

The invention further relates to a process for the preparation of the compounds of the formula I, in which R1, R2, R3 and R4 have the meanings indicated above, and their salts. The process comprises subjecting compounds of the formula II

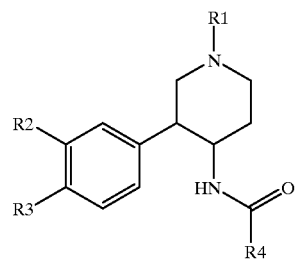

(II)

in which R1, R2, R3 and R4 have the meanings indicated above, to a cyclocondensation reaction and, if desired, then converting the compounds of the formula I obtained into their salts, or, if desired, then converting salts of the compounds of the formula I obtained into the free compounds.

If desired, compounds of the formula I obtained can be converted into further compounds of the formula I by derivatization. For example, the corresponding acids can be obtained from compounds of the formula I in which R4 is a phenyl radical which is substituted by R5 and R6, and R6 is an ester group, by acidic or alkaline hydrolysis, or the corresponding amides can be prepared by reaction with amines of the formula HN(R81)R82, in which R81 and R82 have the meanings indicated above. The reactions are expediently carried out analogously to the methods known to the person skilled in the art, e.g. as described in the following examples.

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxytrichloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling temperature of the solvent or condensing agent used.

Compounds of the formula II in which R1, R2, R3 and R4 have the meanings indicated above are accessible from the corresponding compounds of the formula III

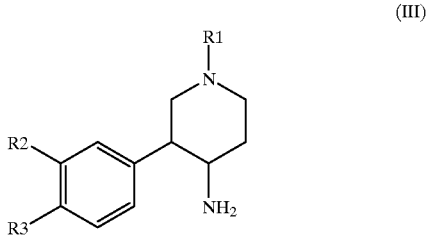

(III)

in which R1, R2 and R3 have the meanings indicated above, by reaction with compounds of the formula R4—CO—X in which R4 has the meaning indicated above and X is a suitable leaving group, preferably a chlorine atom. For example, the benzoylation is carried out as in the following examples according to the Einhorn process, the Schotten-Baumann variant or as described in J. Chem. Soc. (C), 1971, 1805–1808.

The preparation of cis/trans racemate mixtures and of pure cis racemates of compounds of the formula III is described, for example, in U.S. Pat. No. 3,899,494, in DE-A 21 23 328 and in DE-A 16 95 782. Pure cis enantiomers of the compounds of the formula III can be obtained, for example, by the processes as are disclosed in EP 0 247 971 and in DE 42 17 401.

Compounds of the formula R4—CO—X are either known or can be prepared in a known manner.

The substances according to the invention are isolated and purified in a manner known per se, for example by distilling off the solvent in vacuo and recrystallizing the residue obtained from a suitable solvent or subjecting it to one of the customary purification methods, such as, for example, column chromatography on a suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically intolerable salts can be converted into pharmacologically tolerable salts.

The following examples serve to illustrate the invention in greater detail without restricting it. Further compounds of the formula I, whose preparation is not explicitly described, can also be prepared in an analagous manner or in a manner familiar per se to the person skilled in the art using customary process techniques.

In the examples, m.p. stands for melting point, h for hour(s), RT for room temperature, EF for empirical formula, MW for molecular weight, calc. for calculated. The compounds mentioned in the examples and their salts are a preferred subject of the invention.

EXAMPLES

FINAL PRODUCTS 1. (−)-cis-8,9-Dimethoxy-6-(4-methoxycarbonylphenyl)-2-methyl-1,2,3,4,4a,10b-hexahydrobenzo[c][1,6]naphthyridine hydrochloride 2.31 g of (−)-cis-terephthalic acid N-[3-(3,4-dimethoxyphenyl)-1-methylpiperidin-4-yl]amide monomethyl ester are heated to boiling under reflux for 4 h in 25 ml of acetonitrile and 3 ml of phosphorus oxytrichloride. After distilling off the excess phosphorus oxytrichloride, the residue is partitioned between dichloromethane and saturated sodium hydrogencarbonate solution. The organic phase is washed with water, dried over sodium sulfate and concentrated. The solid residue is purified by silica gel chromatography, the main product fraction is separated and this is concentrated. The solid residue is dissolved in a little methanol, and the solution is treated with one equivalent of aqueous HCl and concentrated. The solid residue is recrystallized in methanol/diethyl ether. 1.76 g (70% of theory) of the title compound are obtained as a 1.25-hydrochloride 0.5-hydrate having the m.p. 188–192° C. (unsharp, slow deliquescence).

EF: $C_{23}H_{26}N_2O_4 \times 1.25HCl \times 0.5H_2O$; MW: 449.05

Elemental analysis: Calc.: C, 61.52; H, 6.34; Cl, 9.87; N, 6824. Found: C, 61.52; H, 6.19; Cl, 9.93; N, 623.

Optical rotation: $[\alpha]^{20}_D$ −66° (c=1, methanol).

Starting from the corresponding starting compounds described below, the following title compounds are obtained analogously to Example 1:

2. (−)-cis-8,9-Dimethoxy-6-(3-methoxycarbonylphenyl)-2-methyl-1,2,3,4,4a,10b-hexahydrobenzo[c][1,6]naphthyridine hydrochloride EF: $C_{23}H_{26}N_2O_4 \times 1.1HCl \times 0.23H_2O$; MW: 438.69; m.p. from about 155° C. slow deliquescence; yield: 63% of theory Elemental analysis: Calc.: C, 63.08; H, 6.32; Cl, 8.90; N, 6.40. Found: C, 63.13; H, 6.53; Cl, 8.81; N, 6.53.

Optical rotation: $[\alpha]^{20}_D$ −90.8° (c=1, methanol).

3. (−)-cis-8,9-Dimethoxy-6-(4-isoropoxycarbonylphenyl)-2-methyl-1,2,3,4,4a,10b-hexahydrobenzo[c][1,6]naphthyridine hydrochloride EF: $C_{25}H_{30}N_2O_4 \times 1.15HCl \times 0.8H_2O$; MW: 478.79; m.p. 166–170° C.; yield: 65% of theory;

Elemental analysis: Calc.: C, 62.84; H, 6.88; Cl, 8.53; N, 5.86. Found: C, 62.92; H, 7.06; Cl, 8.44; N, 6.04.

Optical rotation: $[\alpha]^{20}_D$ −40.4° (c=1, methanol).

4. (−)-cis-8,9-Diethoxy-6-(4-methoxycarbonylphenyl)-2-methyl-1,2,3,4,4a,10b-hexahydrobenzo[c][1,6]naphthyridine hydrochloride EF: $C_{25}H_{30}N_2O_4 \times 1.25HCl \times 1.12H_2O$; MW: 485.9; m.p. 143≧148° C.; yield: 76% of theory;

Elemental analysis: Calc.: C, 61.79; H, 6.97; Cl, 8.18; N, 5.76. Found: C, 61.88; H, 6.88; Cl, 8.34; N, 5.70.

Optical rotation: $[\alpha]^{20}_D$ –50.2° (c=1 methanol).

5. (–)-cis-8,9-Diethoxy-6-(4-isopropoxycarbonylphenyl)-2-methyl-1,2,3,4,4a,10b-hexahydrobenzo[c][1,6]naphthyridine hydrochloride EF: $C_{27}H_{34}N_2O_4 \times 1.1HCl \times 0.83H_2O$; MW: 505.64; m.p. 205–209° C., from about 165° C. slow agglutination; yield: 69% of theory;

Elemental analysis: Calc.: C, 64.17; H, 7.33; Cl, 7.72; N, 5.65. Found: C, 64.29; H, 7.37; Cl, 7.60; N, 5.65.

Optical rotation: $[\alpha]^{20}_D$ –47.1° (c=1, methanol).

6. (–)-cis-6-(4-Aminocarbonylphenyl)-8,9-dimethoxyphenyl-2-methyl-1,2,3,4,4a10b-hexahydrobenzo[c][1,6]naphthyridine The title compound from Example 1 is allowed to stand at RT for 48 h in a 1+1 vol. mixture of methanol and conc. ammonia solution. After concentrating completely, the solid residue is recrystallized in a mixture of 1 part by volume of methanol and 10 parts by volume of diethyl ether. 51% of theory of the title compound of m.p. 229–232° C. is obtained.

EF: $C_{22}H_{25}N_3O_3$; MW: 379.46;

Elemental analysis: Calc.: C, 69.64; H, 6.64; N, 11.07. Found: C, 69.41; H, 6.54; N, 11.00.

Optical rotation: $[\alpha]^{20}D$=–104.7° (c=1, methanol).

7. (–)-cis-6-(4-Carboxyphenyl)-8,9-dimethoxyphenyl-2-methyl-1,2,3,4,4a,10b-hexahydrobenzo[c][1,6]naphthyridine The ester group of the title compound from Example 1 is hydrolyzed at RT in a mixture of methanol and 2N sodium hydroxide solution. After hydrolysis is complete, the mixture is neutralized by addition of an appropriate amount of hydrochloric acid and the suspension obtained is largely concentrated (removal of the methanol). The solid residue is suspended using water and filtered off with suction. After thorough washing with water, the filter residue consists of the title compound, which after drying has an m.p. of 237–240° C.

EF: $C_{22}H_{24}N_2O_4 \times 0.5H_2O$; MW: 389.46; yield: 80% of theory;

Elemental analysis: Calc.: C, 67.85; H, 6.47; N, 7.19. Found: C, 68.05; H, 6.62; N, 7.24.

Analogously to Example 7, the following 2 title compounds are obtained by hydrolysis of the corresponding esters described above:

8. (–)-cis-6-(3-Carboxyphenyl)-8,9-dimethoxyphenyl-2-methyl-1,2,3,4,4a,10b-hexahydrobenzo[c][1,6]naphthyridine EF: $C_{22}H_{24}N_2O_4$; MW: 380.45; yield: 76% of theory; m.p. from about 168° slow agglutination, from about 230° C. decomposition.

9. (–)-cis-6-(4-Carboxyphenyl)-8,9-diethoxyphenyl-2-methyl-1,2,3,4,4a,10b-hexahydrobenzo[c][1,6]naphthyridine EF: $C_{24}H_{28}N_2O_4$; MW: 408.50; yield: 88% of theory; m.p.>240° C. (decomposition).

The following title compounds are obtained analogously to Example 1 when the piperidines appropriately substituted in the 4-position are employed as starting compounds for the cyclocondensation. These are obtained in the manner described below for the starting compound A when appropriate terephthalic acid monoamides are employed.

10. (–)-cis-8,9-Diethoxy-6-(4-dimethylaminocarbonylphenyl)-2-methyl-1,2,3,4,4a,10b-hexahydrobenzo[c][1,6]naphthyridine hydrochloride EF: $C_{26}H_{33}N_3O_3 \times HCl \times H_2O$; MW: 490.05; m.p.: 142–150° C. (solid foamed product); yield: 46% of theory;

Elemental analysis: Calc.: C, 63.73; H, 7.40; Cl, 7.23; N, 8.57. Found: C, 64.08; H, 7.32; Cl, 7.48; N, 8.31.

Optical rotation: $[\alpha]^{20}_D$ –28.9° (c=1, methanol).

11. (–)-cis-8,9-Diethoxy-6-(4-diisopropylaminocarbonylphenyl-2-methyl-1,2,3,4,4a,10b-hexahydrobenzo[c][1,6]naphthyridine hydrochloride EF: $C_{30}H_{41}N_3O_3 \times HCl \times 1.4H_2O$; MW: 553.37; m.p.: 164–180° C. (unsharp range); yield: 30% of theory;

Elemental analysis: Calc.: C, 65.12; H, 8.16; Cl, 641; N, 7.59. Found: C, 64.85; H, 8.29; Cl, 6.50; N, 7.66.

Optical rotation: $[\alpha]^{20}_D$ –42.0° (c=1, methanol).

12. (–)-cis-8,9-Dimethoxy-6-(4-diisopropylaminocarbonylphenyl)-2-methyl-1,2,3,4,4a,10b-hexahydrobenzo[c][1,6]naphthyridine hydrochloride EF: $C_{28}H_{37}N_3O_3 \times HCl \times 2.4H_2O$; MW: 542.32; m.p.: 175–185° C. (unsharp range); yield: 24% of theory;

Elemental analysis: Calc.: C, 62.01; H, 7.77; Cl, 6.54; N, 7.75. Found: C, 61.88; H, 7.81; Cl, 6.68; N, 7.73.

Optical rotation: $[\alpha]^{20}_D$ –60.6° (c=1, methanol).

13. (–)-cis-8,9-Dimethoxy-6-(4-dimethylaminocarbonylphenyl)-2-methyl-1,2,3,4,4a,10b-hexahydrobenzo[c][1,6]naphthyridine hydrochloride EF: $C_{24}H_{29}N_3O_3 \times Cl \times 0.6H_2O$; MW: 454.79; m.p.: 226–228° C. (decomposition); yield: 21% of theory;

Elemental analysis: Calc.: C, 63.38; H, 6.92; Cl, 7.80; N, 9.24. Found: C, 63.10; H, 7.13; Cl, 8.12; N, 9.14.

Optical rotation: $[\alpha]^{20}_D$ –58.0.° (c=1, methanol).

14. (+)-cis-8,9-Diethoxy-2-methyl-6-[4-(4-morpholinocarbonyl)phenyl]-1,2,3,4,4a,10b-hexahydrobenzo[c][1,6]naphthyridine hydrochloride EF: $C_{28}H_{35}N_3O_4 \times 1.25HCl \times H_2O$; MW: 541.20; m.p.: 165–170° C. (unsharp range); yield: 45% of theory;

Elemental analysis: Calc.: C, 62.14; H, 7.12; Cl, 8.19; N, 7.76. Found: C, 62.30; H, 7.21; Cl, 7.96; N, 7.35.

Optical rotation: $[\alpha]^{20}D$=+12.4° (c=1, methanol).

15. (+)-cis-8,9-Diethoxy-6-(4-dicyclohexylaminocarbonylphenyl)-2-methyl-1,2,3,4,4a,10b-hexahydrobenzo[c][1,6]naphthyridine hydrochloride EF: $C_{36}H_{49}N_3O_3 \times 1.2HCl \times 1.4H_2O$; MW: 640.78; m.p.: 195–202° C. (unsharp range); yield: 65% of theory;

Elemental analysis: Calc.: C, 67.48; H, 8.34; Cl, 6.64; N, 6.56. Found: C, 67.53; H, 8.16; Cl, 6.62; N, 6.71.

Optical rotation: $[\alpha]^{20}D$=+24.2° (c=1, methanol).

16. (+)-cis-8,9-Diethoxy-6-(4-N-cyclohexyl-N-isopropylaminocarbonylphenyl)-2-methyl-1,2,3,4,4a,10b-hexahydrobenzo[c][1,6]naphthyridine hydrochloride EF: $C_{33}H_{45}N_3O_3 \times 1.25HCl \times 1H_2O$; MW: 595.33; m.p.: 163–195° C. (unsharp range); yield: 57% of theory;

Elemental analysis: Calc.: C, 66.58; H, 8.17; Cl, 7.44; N, 7.06. Found: C, 66.71; H, 8.04; Cl, 7.42; N, 7.25.

Optical rotation: $[\alpha]^{20}D$=+21.6° (c=1, methanol).

17. (+)-cis-8,9-Diethoxy-6-(4-dibutylaminocarbonylphenyl)-2-methyl-1,2,3,4,4a,10b-hexahydrobenzo[c][1,6]naphthyridine hydrochloride EF: $C_{32}H_{45}N_3O_3 \times 2HCl \times 0.9H_2O$; MW: 608.88; m.p.: 144–162° C. (unsharp range; decomposition); yield: 62% of theory;

Elemental analysis: Calc.: C, 63.13; H, 8.08; Cl, 11.65; N, 6.90. Found: C, 63.29; H, 8.18; Cl, 11.61; N, 6.80.

Optical rotation: $[\alpha]^{20}D$=+191.7° (c=1, methanol).

18. (–)-cis-8,9-Diethoxy-6-[4-(hexahydroazepin-1-ylcarbonyl)phenyl]-2-methyl-1,2,3,4,4a,10b-hexahydrobenzo[c][1,6]naphthyridine hydrochloride EF: $C_{30}H_{39}N_3O_3 \times 1.2HCl \times 0.6H_2O$; MW: 544.23; m.p.: 138–154° C. (unsharp range); yield: 58% of theory;

Elemental analysis: Calc.: C, 66.21; H, 7.66; Cl, 7.81; N, 7.72. Found: C, 66.17; H, 7.70; Cl, 7.80; N, 7.71.

Optical rotation: $[\alpha]^{20}_D$ –11.5° (c=1, methanol).

19. (–)-cis-9-Ethoxy-8-methoxy-6-(4-diisopropylaminocarbonylphenyl)-2-methyl-1,2,3,4,4a,10b-hexahydrobenzo[c][1,6]naphthyridine hydrochloride EF: $C_{29}H_{39}N_3O_3 \times HCl \times 0.6H_2O$; MW: 524.92; m.p.: 175–179° C. (unsharp); yield: 67% of theory;
Elemental analysis: Calc.: C, 66.36; H, 7.91; Cl, 6.75; N, 8.01. Found: C, 66.28; H, 7.99; Cl, 6.87; N, 7.97.
Optical rotation: $[\alpha]^{20}_D$–42.7° (c=1,methanol).

20. (–)-cis-8-Ethoxy-9-methoxy-6-(4-diisopropylaminocarbonylphenyl)-2-methyl-1,2,3,4,4a,10b-hexahydrobenzo[c][1,6]naphthyridine hydrochloride
EF: $C_{29}H_{39}N_3O_3 \times 1.03HCl \times 0.94H_2O$; MW: 532.16; m.p.: 176–179° C. (unsharp); yield: 43% of theory;
Elemental analysis: Calc.: C, 65.49; H, 7.94; Cl, 6.87; N, 7.90. Found: C, 65.43; H, 7.71; Cl, 6.86; N, 7.99.
Optical rotation: $[\alpha]^{20}_D$–48.0° (c=1, methanol).

21. (–)-cis-9-Ethoxy-8-methoxy-6-(4-methoxycarbonylphenyl)-2-methyl-1,2,3,4,4a,10b-hexahydrobenzo[c][1,6]naphthyridine hydrochloride
EF: $C_{24}H_{28}N_2O_4 \times 1.05HCl \times 1.27\ H_2O$; MW:; m.p.: 150–160° C. (sintering, unsharp range); yield: 89% of theory;
Elemental analysis: Calc.: C, 61.37; H, 6.78; Cl, 7.92; N, 5.96. Found: C, 61.39; H, 6.77; Cl, 7.93; N, 5.94.
Optical rotation: $[\alpha]^{20}_D$–84.3° (c=1, methanol).

22. (–)-cis-9-Ethoxy-8-methoxy-6-(3-methoxycarbonylphenyl)-2-methyl-1,2,3,4,4a,10b-hexahydrobenzo[c][1,6]naphthyridine hydrochloride
EF: $C_{24}H_{28}N_2O_4 \times HCl \times 0.66H_2O$; MW: 456.82; m.p.: sintering from about 140° C., slow melting with decomposition up to about 150° C.; yield: 88% of theory;
Elemental analysis: Calc.: C, 63.11; H, 6.69; Cl, 7.76; N, 6.13. Found: C, 62.98; H, 6.78; Cl, 7.89; N, 6.07.
Optical rotation: $[\alpha]^{20}_D$–143.1° (c=1, methanol).

23. (–)-cis-9-Ethoxy-8-methoxy-6-(4-dibutylaminocarbonylphenyl)-2-methyl-1,2,3,4,4a,10b-hexahydrobenzo[c][1,6]naphthyridine hydrochloride
EF: $C_{31}H_{43}N_3O_3 \times 1.1HCl \times 1.17H_2O$; MW: 566.82; m.p.: 104–112° C. (solid foamed product, slow deliquescence); yield: 60% of theory;
Elemental analysis: Calc.: C, 65.68; H, 8.26; Cl, 6.88; N, 7.41. Found: C, 65.80; H, 8.09; Cl, 6.97; N, 7.49.
Optical rotation: $[\alpha]^{20}_D$–16.2° (c=1, methanol).

24. (–)-cis-9-Ethoxy-8-methoxy-6-[4-(hexahydroazepin-1-yl-carbonyl)phenyl]-2-methyl-1,2,3,4,4a,10b-hexahydrobenzo[c][1,6]naphthyridine
EF: $C_{29}H_{37}N_3O_3$; MW: 475.65; m.p.: 135–142° C. (unsharp range, sintering from about 125° C.); yield: 66% of theory;
Elemental analysis: Calc.: C, 73.23; H, 7.84; N, 8.83. Found: C, 73.02; H, 8.08; N, 8.67.
Optical rotation: $[\alpha]^{20}_D$–72.5° (c=1, methanol).

25. (–)-cis-9-Ethoxy-8-methoxy-6-[4-(piperidin-1-yl-carbonyl)phenyl]-2-methyl-1,2,3,4,4a,10b-hexahydrobenzo[c][1,6]naphthyridine hydrochloride
EF: $C_{28}H_{25}N_3O_3 \times 0.4H_2O$; MW: 468.82; m.p.: 79–82° C. (unsharp range); yield: 43% of theory;
Elemental analysis: Calc.: C, 71.70; H, 7.70; N, 8.96. Found: C, 71.78; H, 7.71; N, 8.97.
Optical rotation: $[\alpha]^{20}_D$–77.2° (c=1, methanol).

Analogously to Example 7, the following 2 title compounds are obtained by hydrolysis of the corresponding esters described above.

26. (–)-cis-6-(4-carboxyphenyl)-9-ethoxy-8-methoxyphenyl-2-methyl-1,2,3,4,4a,10b-hexahydrobenzo[c][1,6]naphthyridine
EF: $C_{23}H_{26}N_2O_4 \times 1.1H_2O$; MW: 414.29; m.p.: 240–242° C. (decomposition with red coloration); yield: 91% of theory;
Elemental analysis: Calc.: C, 66.68; H, 6.86; N, 6.76. Found: C, 66.81; H, 6.75; N, 6.70.
Optical rotation: $[\alpha]^{20}_D$–109.7° (c=1, methanol+1.0 equivalent of 0.1N NaOH).

27. (–)-cis-6-(3-Carboxyphenyl)-9-ethoxy-8-methoxyphenyl-2-methyl-1,2,3,4,4a,10b-hexahydrobenzo[c][1,6]naphthyridine
EF: $C_{23}H_{26}N_2O_4 \times 0.54H_2O$; MW: 404.17; m.p.: 158–170° C. (decomposition); yield: 83% of theory;
Elemental analysis: Calc.: C, 68.36; H, 6.75; N, 6.93. Found: C, 68.25; H, 6.86; N, 6.96.
Optical rotation: $[\alpha]^{20}_D$–150.7° (c=1, methanol+1.0 equivalent of 0.1N NaOH).

STARTING COMPOUNDS

A. (–)-cis-Terephthalic acid N-[3-(3,4-dimethoxyphenyl)-1-methylpiperidin-4-yl]amide monomethyl ester A solution of monomethyl terephthaloyl chloride (prepared from 2.2 g of monomethyl terephthalate and thionyl chloride) in 5 ml of dichloromethane is added dropwise at RT in the course of 10 min. to a solution of 3 g of (–)-cis-4-amino-3-(3,4-dimethoxyphenyl)-1-methylpiperidine (prepared by extraction of the free base with dichloromethane after treatment of the corresponding dihydrochloride ($[\alpha]^{20}D$=–57.1°, c=1, methanol) with dilute sodium hydroxide solution) in 10 ml of dichloromethane and 1.9 ml of triethylamine. After stirring for about 2 h, the mixture is extracted with about 50 ml of saturated sodium hydrogencarbonate solution, and the organic phase is washed a further two times with 50 ml of water each time and dried over sodium sulfate. The viscous residue remaining after concentration is purified by column chromatography. The main product fraction concentrated in vacuo affords a solid foaming residue which is recrystalized in a mixture of methanol and diethyl ether (about 1+1 vol.). 2.3 g of the title compound having the m.p. 151–152° C. are obtained; yield: 47% of theory; EF: $C_{23}H_{28}N_2O_5$; MW: 412.48.
Elemental analysis: Calc. C, 66.97; H, 6.84; N, 6.79. Found C, 66.82; H, 6.97; N, 6.97.
Optical rotation: $[\alpha]^{22}_D$–74.9° (c=1, methanol).

Starting from the corresponding starting compounds, the following title compounds are obtained analogously to the procedure according to Example A:

B. (–)-cis-Isophthalic acid N-[3-(3,4dimethoxyphenyl)-1-methylpiperidin-4-yl]amide monomethyl ester
EF: $C_{23}H_{28}N_2O_5$; MW: 412.49; yield: 63% of theory; m.p.: 122–123° C.;
Optical rotation: $[\alpha]^{20}_D$–30.6° (c=1, methanol).

C. (–)-cis-Terephthalic acid N-[3-(3,4-dimethoxyphenyl)-1-methylpiperidin-4-yl]amide monoisopropyl ester
EF: $C_{25}H_{32}N_2O_5$; MW: 440.54; yield: 60% of theory; m.p.: 136–142° C. (unsharp);
Optical rotation: $[\alpha]^{20}_D$–48.2° (c=1, methanol).

D. (–)-cis-Terephthalic acid N-[3-(3,4-diethoxyphenyl)-1-methylpiperidin-4-yl]amide monomethyl ester
EF: $C_{25}H_{32}N_2O_5$; MW: 440.54; yield: 55% of theory; m.p.: 169–173° C. (unsharp);
Optical rotation: $[\alpha]^{20}_D$–66.4° (c=1, methanol).

The title compound is obtained by the process described in Example A when (–)-cis-4-amino-3(3,4-diethoxyphenyl)-1-methylpiperidine having the optical rotation $[\alpha]^{20}_D$–35.1° (dihydrochloride, solid foamed crude product, c=1, methanol) is employed as the amine component.

E. (–)-cis-Terephthalic acid N-[3-(3,4-diethoxyphenyl)-1-methylpiperidin-4-yl]amide monoisopropyl ester
EF: $C_{27}H_{36}N_2O$; MW: 468.6; yield: 63% of theory; m.p.: 119–126° C. (unsharp);
Optical rotation: $[\alpha]^{20}_D$–51.5° (c=1, methanol).

F. (−)-cis-4-Amino-3-(3,4-diethoxyphenyl)-1-methylpiperidine dihydrochloride

The title compound is obtained analogously to the process described in DE 42 17 401 when the corresponding 3,4-diethoxy compounds are employed in the examples described there.

EF: $C_{16}H_{26}N_2O_2 \times 2HCl$; MW: 351.32; obtained as a solid foamed crude product; m.p.: shrinkage and slow deliquescence from about 120° C., unsharp melting range up to about 150° C.;

Optical rotation: $[\alpha]^{20}_D$ −35.1° (c=1, methanol).

G. (−)-cis-N-[3-(3,4-Diethoxyphenyl)-1-methylpiperidin-4-yl]-4-(morpholine-4-carbonyl)benzamide EF: $C_{28}H_{37}N_3O_5$; MW: 495.6; yield: 71% of theory: m.p.: 178–179° C.;

Optical rotation: $[\alpha]^{20}_D$ −57.3° (c=1, methanol).

H. (−)-cis-Terephthalic acid N,N-dibutyl-N'-[3-(3,4-diethoxyphenyl)-1-methylpiperidin-4-yl]-diamide EF: $C_{32}H_{47}N_3O_4 \times 0.25H_2O$; MW: 537.75; yield: 76% of theory; m.p.: 115–120° C.;

Optical rotation: $[\alpha]^{20}_D$ −57.0° (c=1, methanol).

I. (−)-cis-Terephthalic acid N-cyclohexyl-N'-[3-(3,4-diethoxyphenyl)-1-methylpiperidin-4-yl]-N-isopropyldiamide EF: $C_{33}H_{47}N_3O_4$; MW: 549.76; yield: 66% of theory; m.p.: 59–64° C. (unsharp range, solidified foam);

Optical rotation: $[\alpha]^{20}_D$ −39.9° (c=1, methanol).

J. (−)-cis-Terephthalic acid N,N-diisopropyl-N'-[3-(3-ethoxy-4-methoxyphenyl)-1-methylpiperidin-4-yl] diamide CH: $C_{29}H_{41}N_3O_4$; MW: 495.67; yield: 91% of theory; m.p.: 75–82° C. (unsharp range, solidified foam);

Optical rotation: $[\alpha]^{20}_D$ −60.1° (c=1, methanol).

K. (−)-cis-Terephthalic acid N,N-diisopropyl-N'-[3-(4-ethoxy-3-methoxyphenyl)-1-methylpiperidin-4-yl] diamide EF: $C_{29}H_{41}N_3O_4$; MW: 495.67; yield: 89% of theory; m.p.: 72–80° C. (unsharp range, solidified foam).

L. (−)-cis-Terephthalic acid N,N-dibutyl-N'-[3-(3-ethoxy-4-methoxyphenyl)-1-methylpiperidin-4-yl]diamide EF: $C_{31}H_{45}N_3O_4$; MW: 523.73; yield: 90% of theory; m.p.: 98–102° C.

M. (−)-cis-4-Hexahydroazepine-1-carbonyl)-N-[3-(3-ethoxy-4-methoxyphenyl)-1-piperidin-4-yl]benzamide EF: $C_{29}H_{39}N_3O_4$; MW: 493.66; yield: 98% of theory; m.p.: 63–66° C. (unsharp range, solidified foam).

The following compounds are obtained analogously to the process described in DE 42 17 401 when the corresponding 4-ethoxy-3-methoxy or 3-ethoxy-4-methoxy compounds are employed in the examples described there:

N. (−)-cis-4-Amino-3-(4-ethoxy-3-methoxyphenyl)-1-methylpiperidine dihydrochloride EF: $C_{15}H_{24}N_2O_2 \times 2HCl \times 0.32H_2O$; MW: 343.06; m.p.: 241–243° C.;

Optical rotation: $[\alpha]^{20}_D$ −59.5° (c=1, methanol).

O. (−)-cis-4-Amino-3-(3-ethoxy-4-methoxyphenyl)-1-methylpiperidine dihydrochloride EF: $C_{15}H_{24}N_2O_2 \times 2HCl \times 0.96H_2O$; MW: 354.52; m.p.: 252–254° C.;

Optical rotation: $[\alpha]^{20}_D$ −65.5° (c=1, methanol).

COMMERCIAL UTILITY

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating and cilium-stimulating action but also on account of their respiratory rate—and respiratory drive—increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action, e.g. in the region of the bronchial system, of the blood circulation, and of the efferent urinary passages. Furthermore they have a cilium-frequency increasing action, e.g. in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma); disorders with a reduction of the cilium activity or with increased demands on the ciliar clearance (bronchitis, mucoviscidose); dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (Type I autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps: and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as anti-thrombotic, platelet aggregation-inhibiting substances.

The invention further relates to a method for the treatment of mammals including humans who are suffering from one of the abovementioned diseases. The method comprises administering a therapeutically effective and pharmacologically tolerable amount of one or more of the compounds according to the invention to the sick mammal.

The invention further relates to the compounds according to the invention for use in the treatment and/or prophylaxis of the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their cAMP degradation-inhibiting action, they in this case display a synergistic, superadditive activity. This comes to bear, for example, in their use in combination with PGE2 for the treatment of pulmonary hypertension.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointments bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 10 mg per spray burst. The customary dose in the case of systemic therapy (p.o. or i.v.) is between 0.1 and 200 mg per administration.

BIOLOGICAL INVESTIGATIONS

In the investigation of PDE4 inhibition at the cellular level, the activation of inflammatory cells has particular importance. An example which may be mentioned is the FMLP (N-formylmethionylleucyl-phenylalanine)-induced superoxide production of neutrophilic granulocytes, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and cytokine secretion and the secretion of inflammation-increasing mediators in inflammatory cells, in particular neutrophilic and eosinophilic granulocytes, are those which inhibit PDE4. This isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhäuser Verlag Basel 1991; Schudt C et al., influence of selective phosphodiesterase inhibitors on human neutrophil functions and levels of cAMP and Ca. Naunyn-Schmiedebergs Arch Pharmacol 1991, 344, 682–690; Nielson C P et al., Effects of selective phosphodiesterase inhibitors on polymorphonuclear leukocytes respiratory burst. J Allergy Clin Immunol 1990, 86, 801–808; Schade et al., The specific type 3 and 4 phosphodiesterase inhibitor zardaverdne suppress formation of tumor necrosis factor by macrophages. European Journal of Pharmacology 1993, 230, 9–14).

A. Methodology

1. Inhibition of PDE Isoenzymes

The PDE activity was determined according to Thompson et al. (1) with some modifications (2). The test samples contained 40 mM tris HCl (pH 7.4), 5 mM $MgCl_2$, 0.5 µM cAMP or cGMP, [$^3$H] cAMP or [$^3$H]cGMP (about 50,000 cpm/sample), the PDE isoenzyme-specific additions described in greater detail below, the indicated concentrations of inhibitor and an aliquot of the enzyme solution in a total sample volume of 200 μl. Stock solutions of the compounds to be investigated in DMSO were prepared in concentrations such that the DMSO content in the test samples did not exceed 1% by volume—to avoid an effect on the PDE activity. After preincubation at 37° C. for 5 minutes, the reaction was started by addition of the substrate (cAMP or cGMP). The samples were incubated at 37° C. for a further 15 min. The reaction was terminated by addition of 50 μl of 0.2N HCl. After cooling on ice for 10 minutes and addition of 25 μg of 5'-nucleotidase (snake venom from Crotalus atrox), the mixture was again incubated at 37° C. for 10 min and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolyzed nucleotide in no case exceeded 20% of the original substrate concentration.

PDE1 ($Ca^{2+}$/calmodulin-dependent) from bovine brain: the inhibition of this isoenzyme was investigated in the presence of $Ca^{2+}$ (1 mM) and calmodulin (100 nM) using cGMP as a substrate (3).

PDE2 (cGMP-stimulated) from rat hearts was purified chromatographically [Schudt et al. (4)] and investigated in the presence of cGMP (5 μM) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leukocytes (PMNL) [isolated from leukocyte concentrates, see Schudt et al. (5)] using cAMP as a substrate. The PDE3 inhibitor motapizone (1 μM) was used in order to suppress the PDE3 activity emanating from contaminating blood platelets.

2. Inhibition of the Formation of Reactive Oxygen Species in Human PMNL

The formation of reactive oxygen species determined with the aid of luminol-potentiated chemiluminescence (5) and the isolation of the PMNL from human blood (6) was carried out essentially as described in (5) and (6): equal-size portions (0.5 ml) of the cell suspension ($10^7$ cells/ml) were preincubated at 37° C. for 5 min in the absence or presence of the compounds to be investigated in a buffer solution comprising 140 mM NaCl, 5 mM KCl, 10 mM HEPES, 1 mM $CaCl_2/MgCl_2$, 1 mg/ml of glucose, 0.05% (w/v) BSA (bovine serum albumin), 10 μM luminol and 4 μM microperoxidase. Stock solutions of the compounds to be investigated in DMSO were prepared in concentrations such that the DMSO content in the test samples did not exceed 0.1% by volume—to avoid an effect on PDE activity. After preincubation, the test samples were transferred into the measuring apparatus ["Multi-Biolumnat" LB 9505C from Berthold (Wildbad, Germany)] before stimulation with the receptor agonist FMLP (N-fornylmethionylleucyl phenylalanine, 100 nM). The chemiluminescence was recorded continuously for 3 min; from this the AUC values were calculated.

3. Statistics

The $IC_{50}$ values were determined from the concentration-inhibition curves by nonlinear regression using the GraphPad InPlot™ program (GraphPad Software Inc., Philadelphia, U.S.A.).

4. References (1) Thompson W. J. and Appleman M. M., Assay of cyclic nucleotide phosphodiesterase and resolution of multiple molecular forms of the enzyme; Adv. Cycl. Nucl. Res. 1979, 10, 69–92

(2) Bauer A. C. and Schwabe U., An improved assay of cyclic 3', 5'-nucleotide phosphodiesterase with QAE Sephadex A-25; Naunyn-Schmiedeberg's Arch. Pharmacol. 1980, 311, 193–198

(3) Gietzen K, Sadorf I, and Bader H., A model for the regulation of the calmodulin-dependent enzymes erythrocyte $Ca^{2+}$—transport ATPase and brain phosphodiesterase by activators and inhibitors; Biochem. J. 1982, 207, 541–548.

(4) Schudt C., Winder S., Müller B. and Ukena D., Zardaverine as a selective inhibitor of phosphodiesterase isoenzymes; Biochem. Pharmacol. 1991, 42, 153–162

(5) Schudt C., Winder S., Forderkunz S., Hatzelmann A. and Ullrich V., Influence of selective phosphodiesterase inhibitors on human neutrophil functions and levels of cAMP and Ca;
Naunyn-Schmiedeberg's Arch. Pharmacol. 1991, 344, 682–90

(6) Hatzelmann A. and Ullrich V., Regulation of 5-lipoxygenase activity by the glutathione status in human polymorphonuclear leukocytes; Eur. J. Biochem. 1987, 169, 175–184

B. Results

In Table 1 below, the inhibitory concentrations determined according to Section A1 [inhibitory concentrations as -log $IC_{50}$ (mol/l)] for the compounds according to the invention are indicated for various PDE isoenzymes. The numbers of the compounds correspond to the numbers of the examples.

Table 1

| | [-log $IC_{50}$, mol/l] | | | | |
|---|---|---|---|---|---|
| Compound | PDE5 | PDE4 | PDE3 | PDE2 | PDE1 |
| 3 | | 6.45 | 7.14 | | |
| 4 | 5.45 | 7.54 | 6.67 | 4.80 | <4 |
| 5 | | 7.75 | 7.15 | | |
| 11 | | 7.85 | 7.23 | | |
| 16 | | 7.96 | 6.73 | | |
| 17 | | 7.94 | 6.38 | | |
| 18 | | 7.87 | 6.74 | | |
| 19 | | 8.18 | 7.56 | | |
| 21 | | 7.67 | 6.34 | | |
| 23 | | 8.56 | 6.64 | | |
| 24 | | 8.51 | 7.64 | | |

I claim:

1. A compound of formula I

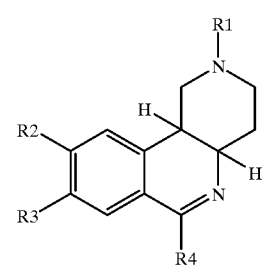

in which

R1 is 1–4C-alkyl,

R2 is hydroxyl, 1–4C-alkoxy, 3–7C-cycloalkoxy, 3–7C-cycloalkylmethoxy or 1–4C-alkoxy which is completely or predominantly substituted by fluorine,

19

R3 is hydroxyl, 1–4C-alkoxy, 3–7C-cycloalkoxy, 3–7C-cycloalkylmethoxy or 1–4C-alkoxy which is completely or predominantly substituted by fluorine, or in which R2 and R3 together are a 1–2C-alkylenedioxy group, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together with the nitrogen atom to which both are bonded, are a 1-pyrrolidinyl, 1-piperidyl, 1-hexahydroazepinyl or 4-morpholinyl radical, or a salt thereof.

2. A compound of formula I according to claim 1, in which

R1 is 1–4C-alkyl,

R2 is 1–4C-alkoxy, 3–7C-cycloalkoxy, 3–7C-cycloalkylmethoxy or 1–2C-alkoxy which is completely or predominantly substituted by fluorine, R3 is 1–4C-alkoxy, 3–7C-cycloalkoxy, 3–7C-cycloalkylmethoxy or 1–2C-alkoxy which is completely or predominantly substituted by fluorine, R4 is a phenyl radical which is substituted by R5 and R6, where R5 is hydrogen, hydroxyl, halogen, nitro, 1–4C-alkyl, trifluoromethyl or 1–4C-alkoxy, R6 is CO—R7 or CO—R8, where R7 is hydroxyl, 1–8C-alkoxy, 3–7C-cycloalkoxy or 3–7C-cycloalkylmethoxy and R8 is N(R81)R82, where R81 and R82 independently of one another are hydrogen, 1–7C-alkyl, 3–7C-cycloalkyl or 3–7C-cycloalkylmethyl, or where R81 and R82, together with the nitrogen atom to which both are bonded, are a 1-piperidyl, 1-hexahydroazepinyl or 4-morpholinyl radical, or a salt thereof.

3. A compound of formula I according to claim 1, in which

R1 is methyl,

R2 is 1–4C-alkoxy, 3–7C-cycloalkoxy or 1–2C-alkoxy which is completely or predominantly substituted by fluorine, R3 is 1–4C-alkoxy, 3–7C-cycloalkoxy or 1–2C-alkoxy which is completely or predominantly substituted by fluorine, R4 is a phenyl radical which is substituted by R5 and R6, where R5 is hydrogen, hydroxyl, 1–4C-alkyl or 1–4C-alkoxy, R6 is CO—R7 or CO—R8, where R7 is hydroxyl, 1–8C-alkoxy or 3–7C-cycloalkoxy and R8 is N(R81)R82, where R81 and R82 independently of one another are hydrogen, 1–7C-alkyl or 3–7C-cycloalkyl, or where R81 and R82, together with the nitrogen atom to which both are bonded, are a 1-piperidyl, 1-hexahydroazepinyl or 4-morpholinyl radical, or a salt thereof.

20

4. A compound of formula I according to claim 1, in which

R1 is methyl,

R2 is methoxy or ethoxy,

R3 is methoxy or ethoxy,

R4 is a phenyl radical which is substituted by R5 and R6, where

R5 is hydrogen,

R6 is CO—R7 or CO—R8, where

R7 is hydroxyl or 1–8C-alkoxy and

R8 is N(R81)R82, where R81 and R82 independently of one another are hydrogen or 1–4C-alkyl or 5—7C-cycloalkyl, or where R81 and R82, together with the nitrogen atom to which both are bonded, are a 1-piperidyl, 1-hexahydroazepinyl or 4-morpholinyl radical, or a salt thereof.

5. A compound of formula I according to claim 1, in which

R1 is methyl,

R2 is ethoxy,

R3 is methoxy or ethoxy,

R4 is a phenyl radical which is substituted by R5 and R6, where

R5 is hydrogen,

R6 is CO—R7 or CO—R8, where

R7 is 1–4C-alkoxy and

R8 is N(R81)R82, where R81 and R82 independently of one another are 1–4C-alkyl or 5–7C-cycloalkyl, or where R81 and R82, together with the nitrogen atom to which both are bonded, are a 1-piperidyl or 1-hexahydroazepinyl radical, or a salt thereof.

6. A compound of formula I according to claim 1, in which the hydrogen atoms in positions 4a and 10 b are in the cis position relative to one another, or a salt thereof.

7. A compound of formula I according to claim 1, which in the positions 4a and 10b have the same absolute configuration as the compound (−)-cis-4-amino-3-(3,4-dimethoxyphenyl)-1-methylpiperidine dihydrochloride having the optical rotation $[\alpha]^{22}_D$ –57.1 ° (c=1, methanol).

8. A compound selected from the group consisting of cis-8,9-Diethoxy-6-(4-isopropoxycarbonylphenyl)-2-methyl-1,2,3,4,4a,10b-hexahydrobenzo[c][1,6]naphthyridine;

cis-8,9-Diethoxy-6-(4-diisopropylaminocarbonylphenyl-2-methyl-1,2,3,4,4a,10b-hexahydrobenzo[c][-1,6]naphthyridine;

cis-8,9-Diethoxy-6-(4-N-cyclohexyl-N-isopropylaminocarbonylphenyl)-2-methyl-1,2,3,4,4a,10b-hexahydrobenzo[c][1,6]naphthyridine;

cis-8,9-Diethoxy-6-(4-dibutylaminocarbonylphenyl)-2-methyl-1,2,3,4,4a,10b-hexahydrobenzo[c][-1,6]naphthyridine;

cis-8,9-Diethoxy-6-[4-(hexahydroazepin-1 -ylcarbonyl)phenyl]-2-methyl-1,2,3,4,4a,10b-hexahydrobenzo[c][1,6]naphthyridine;

cis-8,9-Diethoxy-6-[4-(piperidin-1 -ylcarbonyl)phenyl]-2-methyl-1,2,3,4,4a,10b-hexahydrobenzo[c][1,6]-naphthyridine;

cis-9-Ethoxy-8-methoxy-6-(4-diisopropylaminocarbonylphenyl)-2-methyl-1,2,3,4,4a,10b-hexahydrobenzo[c][1,6]naphthyridine;

cis-9-Ethoxy-8-methoxy-6-(4-dibutylaminocarbonylphenyl)-2-methyl-1,2,3,4,4a,10b-hexahydrobenzo[c][1,6]naphthyridine:

cis-9-Ethoxy-8-methoxy-6-[4-(hexahydroazepin-1-ylcarbonyl)phenyl]-2-methyl-1,2,3,4,4a,10b-hexahydrobenzo[c][1,6]naphthyridine;

cis-9-Ethoxy-8-methoxy-6-[4-(piperidin-1-ylcarbonyl)phenyl]-2-methyl-1,2,3,4,4a,10b-hexahydrobenzo[c][1,6]naphthyridine and a salt thereof.

9. A medicament composition comprising a customary pharmaceutical auxiliary and/or excipient and an effective amount of a compound of formula I according to claim 1 or a pharmaceutically acceptable salt thereof.

10. In a method of producing a medicament composition comprising a customary pharmaceutical auxiliary or excipient and an effective amount of active ingredient for treating an airway disorder or an amenable dermatosis, the improvement wherein the active ingredient is a compound of formula I according to claim 1 or a pharmaceutically acceptable salt thereof.

11. In a method for treating an airway disorder or an amenable dermatosis which comprises administering an effective amount of active ingredient to a subject in need of such treatment, the improvement wherein the active ingredient is a compound of formula I according to claim 1 or a pharmaceutically acceptable salt thereof.

12. A compound of formula I according to claim 5, in which $R1$ is methyl, $R2$ is ethoxy, $R3$ is methoxy, $R4$ is a phenyl radical which is substituted by $R5$ and $R6$, where $R5$ is hydrogen, $R6$ is CO—$R8$, where $R8$ is N($R81$)$R82$ and $R81$ and $R82$ are isopropyl, or a salt thereof.

13. The compound according to claim 7, which is (−)-cis-9-ethoxy-8-methoxy-6-(4-diisopropylaminocarbonylphenyl)-2-methyl-1,2,3,4,4a,10b-hexahydrobenzo[c][1,6]naphthyridine hydrochloride.

\* \* \* \* \*

UNITED STATES PATENT AND TRADEMARK OFFICE
CERTIFICATE OF CORRECTION

PATENT NO. : 6,008,215
DATED : December 28, 1999
INVENTOR(S) : Dieter FLOCKERZI

It is certified that error appears in the above-identified patent and that said Letters Patent is hereby corrected as shown below:

Title page, under item [30], "Nov. 13, 1996 [DE] Germany" should read --Nov. 13, 1996 [EP] European Pat. Off.--

UNITED STATES PATENT AND TRADEMARK OFFICE
CERTIFICATE OF CORRECTION

PATENT NO. : 6,008,215
DATED : December 28, 1999
INVENTOR(S) : FLOCKERZI

It is certified that error appears in the above-identified patent and that said Letters Patent is hereby corrected as shown below:

Column 4, line 41, "i4C-alkoxy" should read --1-4C-alkoxy--; line 63, "4morpholinyl" should read --4-morpholinyl--. Column 5, line 4, "R6,," should read --R6,--; line 26, "-5-7C" should read --5-7-C--; line 58, "$[\alpha]^{22}{}_D=57.1°$" should read --$[\alpha]^{22}_D = -57.1°$--. Column 6, line 5, "[c]-[1,6]" should read --[c][1,6]--. Column 8, line 6, "analagous" should read --analogous--; line 39, "6824" should read --6.24--, and "623" should read --6.23--; line 40, "$[\alpha]^{20}{}_D-66°$" should read --$[\alpha]^{20}_D = -66°$--; line 52, "$[\alpha]^{20}{}_D-90.8$" should read --$[\alpha]^{20}_D = -90.8$--; line 53, "isoropoxycarbonylphenyl" should read --isopropoxycarbonylphenyl--; line 60, "$[\alpha]^{20}{}_D-40.4°$" should read --$[\alpha]^{20}_D = -40.4°$--; line 65, "143 ≥ 148°C" should read --143 - 148°C--. Column 9, line 1, "$[\alpha]^{20}{}_D-50.2°$" should read --$[\alpha]^{20}_D = -50.2°$--; line 10, "$[\alpha]^{20}{}_D-47.1°$" should read --$[\alpha]^{20}_D = -47.1°$--; line 12, "4a10b" should read --4a,10b--; line 23, "$[\alpha]^{20}D=-104.7°$" should read --$[\alpha]^{20}_D = -104.7°$--. Column 10, line 1, "$[\alpha]^{20}{}_D-28.9°$" should read --$[\alpha]^{20}_D = -28.9°$--; line 7, "641" should read --6.41--; line 8, "$[\alpha]^{20}{}_D-42.0°$" should read --$[\alpha]^{20}_D = -42.0°$--; line 16, "$[\alpha]^{20}{}_D-60.6°$" should read --$[\alpha]^{20}_D = -60.6°$--; line 24, "$[\alpha]^{20}{}_D-58.0°$" should read --$[\alpha]^{20}_D = -58.0°$--; line 31, "$[\alpha]^{20}D=+12.4°$" should read --$[\alpha]^{20}_D = +12.4°$--; line 39, "$[\alpha]^{20}D=+24.2°$" should read --$[\alpha]^{20}_D = +24.2°$--; line 47, "$[\alpha]^{20}D=+21.6°$" should read --$[\alpha]^{20}_D = +21.6°$--; line 56, "$[\alpha]^{20}D=+191.7°$" should read --$[\alpha]^{20}_D = +191.7°$--; line 64, "$[\alpha]^{20}{}_D-11.5°$" should read --$[\alpha]^{20}_D = -11.5°$--.

UNITED STATES PATENT AND TRADEMARK OFFICE
CERTIFICATE OF CORRECTION

PATENT NO. : 6,008,215

DATED : December 28, 1999

INVENTOR(S) : FLOCKERZI

It is certified that error appears in the above-identified patent and that said Letters Patent is hereby corrected as shown below:

Column 11, line 5, "$[\alpha]^{20}_D$-42.7°" should read --$[\alpha]^{20}_D = -42.7°$--; line 12, "$[\alpha]^{20}_D$-48.0°" should read --$[\alpha]^{20}_D = -48.0°$--; line 21, "$[\alpha]^{20}_D$-84.3°" should read --$[\alpha]^{20}_D = -84.3°$--; line 30, "$[\alpha]^{20}_D$-143.1°" should read --$[\alpha]^{20}_D = -143.1°$--; line 39, "$[\alpha]^{20}_D$-16.2°" should read --$[\alpha]^{20}_D = -16.2°$--; line 48, "$[\alpha]^{20}_D$-72.5°" should read --$[\alpha]^{20}_D = -72.5°$--; line 56, "$[\alpha]^{20}_D$-77.2°" should read --$[\alpha]^{20}_D = -77.2°$--. Column 12, line 1, "$[\alpha]^{20}_D$-109.7°" should read --$[\alpha]^{20}_D = -109.7°$--; line 10, "$[\alpha]^{20}_D$-150.7°" should read --$[\alpha]^{20}_D = -150.7°$--; line 23, "$[\alpha]^{20}D$=-57.1°" should read --$[\alpha]^{20}_D = -57.1°$--; line 39, "$[\alpha]^{22}_D$-74.9°" should read --$[\alpha]^{22}_D = -74.9°$--; line 43, "3,4" should read --3,4- --; line 47, "$[\alpha]^{20}_D$-30.6°" should read --$[\alpha]^{20}_D = -30.6°$--; line 52, "$[\alpha]^{20}_D$-48.2°" should read --$[\alpha]^{20}_D = -48.2°$--; line 57, "$[\alpha]^{20}_D$-66.4°" should read --$[\alpha]^{20}_D = -66.4°$--; line 59, "3(3,4" should read --3-(3,4--; line 60, "$[\alpha]^{20}_D$-35.1°" should read --$[\alpha]^{20}_D = -35.1°$--; line 65, $C_{27}H_{36}N_2O$" should read --$C_{27}H_{36}N_2O_5$--; line 67, "$[\alpha]^{20}_D$-51.5°" should read --$[\alpha]^{20}_D = -51.5°$--. Column 13, line 11, "$[\alpha]^{20}_D$-35.1°" should read --$[\alpha]^{20}_D = -35.1°$--; line 16, "$[\alpha]^{20}_D$-57.3°" should read --$[\alpha]^{20}_D = -57.3°$--; line 21, "$[\alpha]^{20}_D$-57.0°" should read --$[\alpha]^{20}_D = -57.0°$--; line 27, "$[\alpha]^{20}_D$-39.9°" should read --$[\alpha]^{20}_D = -39.9°$--; line 33, "$[\alpha]^{20}_D$-60.1°" should read --$[\alpha]^{20}_D = -60.1°$--; line 55, "$[\alpha]^{20}_D$ -59.5°" should read --$[\alpha]^{20}_D = -59.5°$--; line 60, "$[\alpha]^{20}_D$ -65.5°" should read --$[\alpha]^{20}_D = -65.5°$--.

UNITED STATES PATENT AND TRADEMARK OFFICE
CERTIFICATE OF CORRECTION

PATENT NO. : 6,008,215
DATED : December 28, 1999
INVENTOR(S) : FLOCKERZI

It is certified that error appears in the above-identified patent and that said Letters Patent is hereby corrected as shown below:

Column 14, line 3, "rate—and respiratory drive—increasing" should read --rate- and respiratory drive-increasing--. Column 18, line 7, "$Ca^{2+}$—transport" should read --$Ca^{2+}$-transport--. Column 20, line 44, "$[\alpha]^{22}_D$-57.1°" should read --$[\alpha]^{22}_D = -57.1°$--; line 49, "diisopropylaminocarbonylphenyl-" should read --diisopropylaminocarbonylphenyl)--; line 50, "[c][-1,6]" should read --[c][1,6]--; line 56, "[c][-1,6]" should read --[c][1,6]--.

Signed and Sealed this

Second Day of January, 2001

Attest:

Q. TODD DICKINSON

*Attesting Officer*          *Commissioner of Patents and Trademarks*